US008383688B2

(12) United States Patent
Lo et al.

(10) Patent No.: US 8,383,688 B2
(45) Date of Patent: Feb. 26, 2013

(54) PRODUCTS WITH WATER CLUSTERS

(75) Inventors: Shui Yin Lo, Pasadena, CA (US); David Gann, Holden, MO (US); Geng Xu, Holden, MO (US)

(73) Assignee: D & Y Laboratories, Las Vegas, NV (US)

( * ) Notice: Subject to any disclaimer, the term of this patent is extended or adjusted under 35 U.S.C. 154(b) by 201 days.

(21) Appl. No.: 12/592,877

(22) Filed: Dec. 3, 2009

(65) Prior Publication Data
US 2011/0218251 A1 Sep. 8, 2011

Related U.S. Application Data

(60) Provisional application No. 61/200,821, filed on Dec. 4, 2008, provisional application No. 61/200,823, filed on Dec. 4, 2008, provisional application No. 61/200,824, filed on Dec. 4, 2008, provisional application No. 61/200,825, filed on Dec. 4, 2008, provisional application No. 61/210,064, filed on Mar. 14, 2009, provisional application No. 61/210,065, filed on Mar. 14, 2009, provisional application No. 61/217,604, filed on Jun. 2, 2009, provisional application No. 61/217,605, filed on Jun. 2, 2009, provisional application No. 61/217,680, filed on Jun. 3, 2009.

(51) Int. Cl.
*A61K 47/00* (2006.01)
*C10L 1/32* (2006.01)
*A23D 9/013* (2006.01)
*C01B 5/00* (2006.01)

(52) U.S. Cl. ....... 514/769; 44/301; 426/531; 423/580.1; 977/832

(58) Field of Classification Search .................. 514/769; 44/301; 426/531; 423/580.1; 977/832
See application file for complete search history.

(56) References Cited

U.S. PATENT DOCUMENTS

| | | | |
|---|---|---|---|
| 5,800,576 A | 9/1998 | Johnson | 44/301 |
| 5,997,590 A | 12/1999 | Johnson | 44/301 |
| 6,487,994 B2 | 12/2002 | Ahern | 123/25 R |
| 2004/0025416 A1 | 2/2004 | Sato | 44/301 |
| 2005/0270896 A1 | 12/2005 | Oogawara | 366/127 |
| 2006/0110418 A1 | 5/2006 | Johnson | 424/401 |

FOREIGN PATENT DOCUMENTS

| | | |
|---|---|---|
| JP | 19913360930 | 6/1993 |
| JP | 07-068266 | 3/1995 |
| JP | 10180263 | 7/1998 |
| JP | 2005-349390 A | 12/2005 |
| WO | WO 2009/049120 | 4/2009 |

OTHER PUBLICATIONS

Ingrid M. Quintana, et al Determination of the Structure and Stability of Water Clusters Using Temperature Dependent Techniques, Chemical Physics Letters, May 1, 1988, vol. 287.
Tomonori, Ohba, et al, Water Cluster Growth in Hydrophobic, Solid Nanospaces, Chemistry A. European Journal, Jun. 1, 2005, vol. 11 pp. 4890-4894 which is reference D5.
B. Bonavita, S.Y.Lo. Proceedings of First International Conference on Physical Chemical and Biological properties of stable water clusters. World Scientific. 1997.

*Primary Examiner* — Raymond Henley, III
(74) *Attorney, Agent, or Firm* — Henry M. Feiereisen

(57) ABSTRACT

A product has solid stable water clusters including a plurality of water molecules connected with one another by electrical dipole interaction via internal electric field of ions and having a permanent electric dipole moment with an electrical field surrounding the solid stable water clusters.

16 Claims, 16 Drawing Sheets

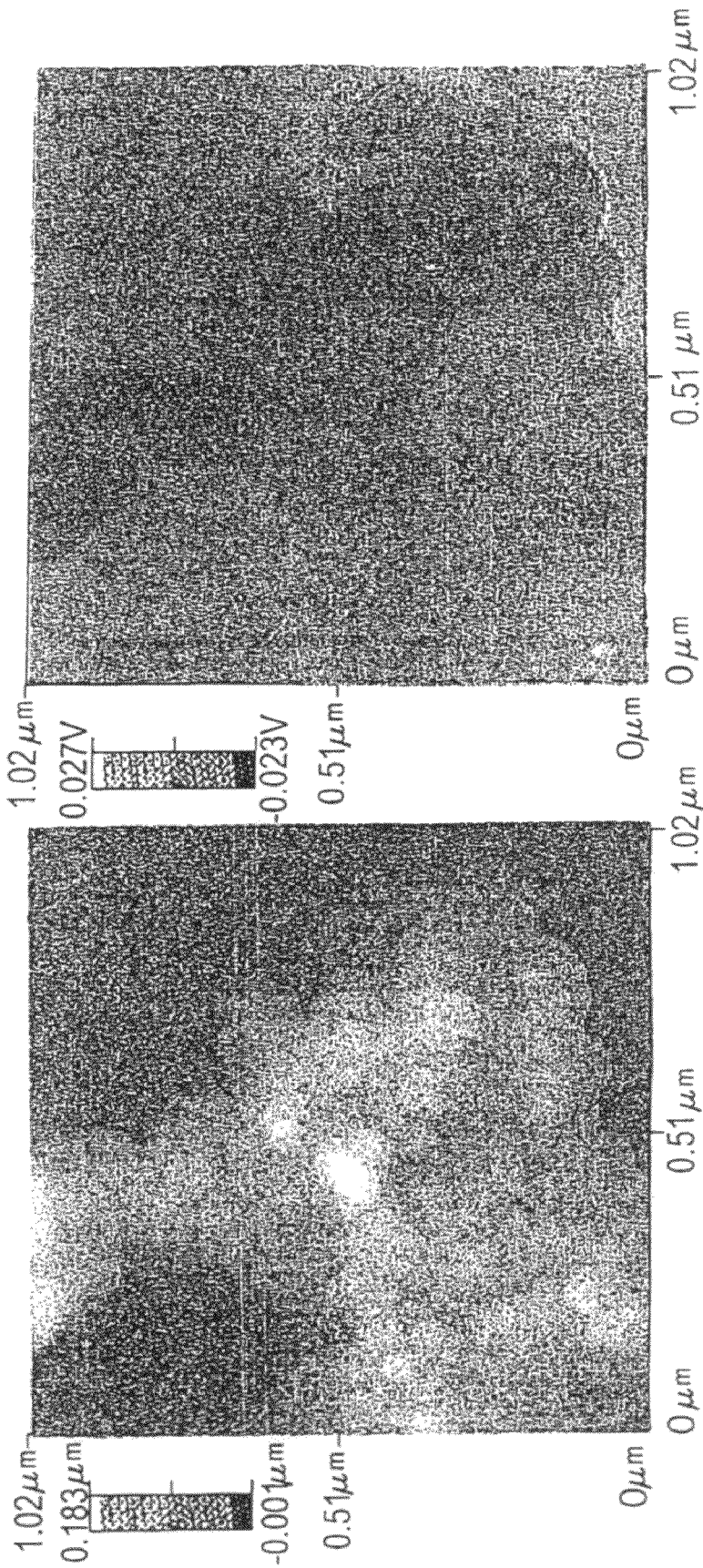

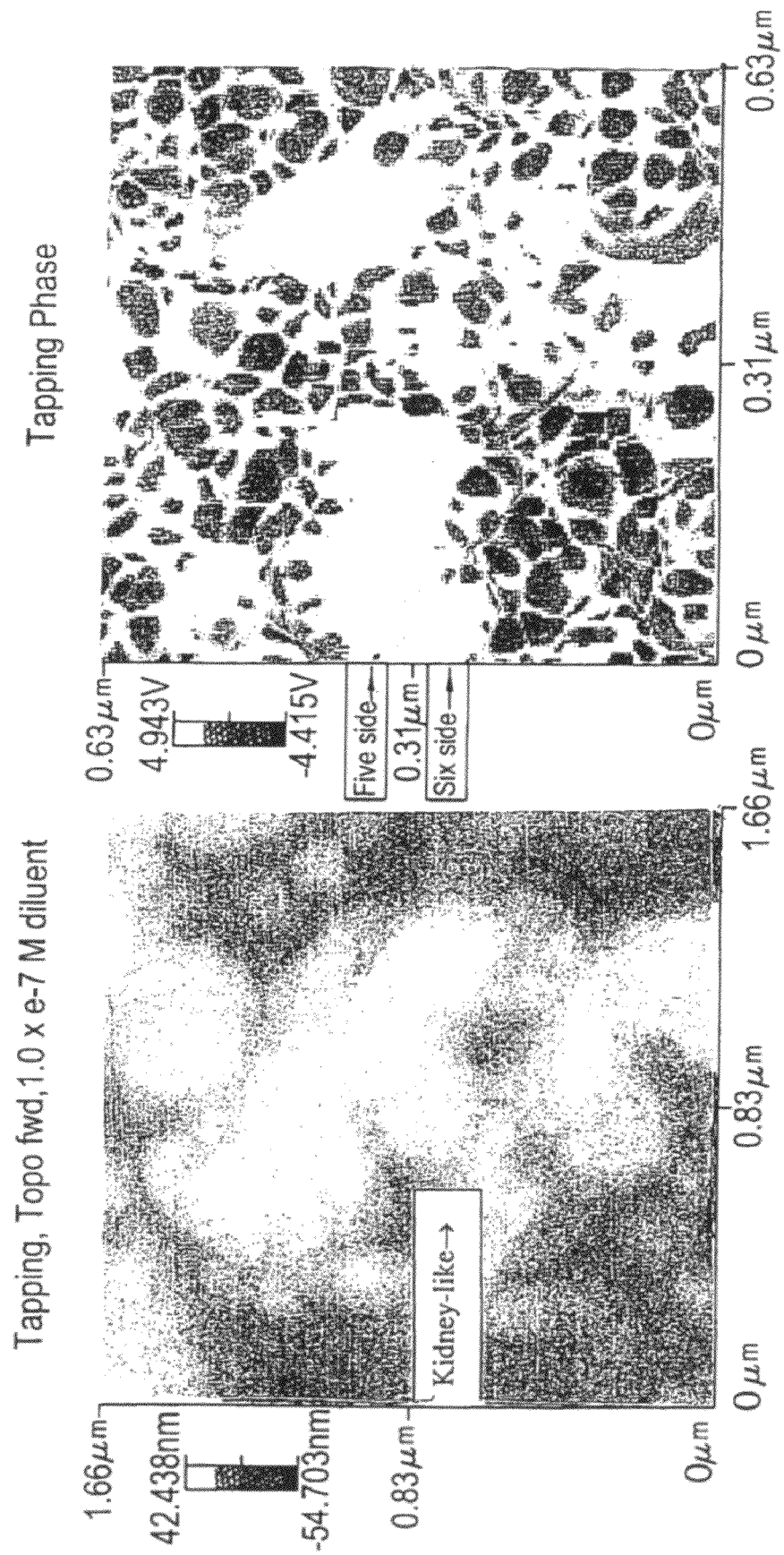

PRODUCTS WITH WATER CLUSTERS

CROSS-REFERENCE TO RELATED APPLICATIONS

This patent application contains subject matter of patent applications.
Ser. No. 61/200,821 filed on Dec. 4, 2008;
Ser. No. 61/200,823 filed on Dec. 4, 2008;
Ser. No. 61/200,824 filed on Dec. 4, 2008;
Ser. No. 61/200,825 filed on Dec. 4, 2008;
Ser. No. 61/210,064 filed on Mar. 14, 2009;
Ser. No. 61/210,065 filed on Mar. 14, 2009;
Ser. No. 61/210,065 filed on Mar. 14, 2009;
Ser. No. 61/217,604 filed on Jun. 2, 2009;
Ser. No. 61/217,605 filed on Jun. 2, 2009;
Ser. No. 61/217,680 filed on Jun. 3, 2009,
which are incorporated here by reference thereto and which constitute the basis for claim to priority of this application.

BACKGROUND OF THE INVENTION

The present invention relates to water clusters and products containing them.

Water clusters and methods of their manufacture and use are known in the art.

They are disclosed for example in Proceedings of First International Conference of the Physical, Chemical and Biological Properties of Stable Water Clusters, edited by B. Bonavita, S. Y. Lo, World Scientific 1997, and in U.S. Pat. Nos. 5,800,576; 5,997,590; U.S. patent application publication 2006/0110418, international patent application publication WO 2009/04912, U.S. patent application publication 2005/0270896, U.S. Pat. No. 6,487,994, U.S. patent application publication 2004/0025416.

It is believed that the known water clusters and products containing them can be further improved.

SUMMARY OF THE INVENTION

Accordingly, it is an object of the present invention to provide improved products containing water clusters.

In keeping with these objects and with others which will become apparent hereinafter, one feature of the present invention resides, briefly stated, in a product, comprising solid stable water clusters including a plurality of water molecules connected with one another by electrical dipole interaction via internal electric field of ions and having a permanent electric dipole moment with an electrical field surrounding the solid stable water clusters.

The stable water clusters have nanometer sizes.

In accordance with the present invention resides the solid stable water clusters are stable under normal room and atmospheric pressure.

In accordance with the present invention a product can contains water with solid stable water clusters in the water.

In accordance with the present invention a product can contains a petroleum component with said solid stable water clusters, wherein the petroleum component can be a component selected from the group consisting of gas, diesel, and natural gas.

A further feature of the present invention resides that in a product can contain a skin care component with the solid stable water clusters contained in it.

In accordance with the product contains a component providing health benefits, with stable solid water clusters contained in it, and the component providing health benefits can be a component selected from the group consisting of vitamins, minerals, hormones and extracts.

A further feature of the present invention resides in that the product can contains solid stable water clusters in form of an emulsion that contains a suspension of small water droplets that include said solid stable water clusters.

That the solid stable water clusters have a ring-shaped structure, selected from the group consisting of pentagon, a hexagon, and a rectangle.

A plurality of ring-shaped structures of said solid stable water clusters can be joined together to form a larger structures of said solid stable water clusters.

In accordance with a further feature of the present invention a solid stable water clusters can be arranged in a form of a double helix.

The solid stable water clusters can be produced by connecting a plurality of water molecules with one another by electrical dipole interaction via internal electric fields of ions to provide the solid stable water clusters having a permanent electrical dipole moment and nanometers sizes.

The production process can include multiple dilution of a material with pure water.

BRIEF DESCRIPTION OF THE DRAWINGS

FIGS. 1 and 2 are atomic force microscope pictures of solid stable water clusters;

FIGS. 14-16 are atomic force microscope pictures of solid stable water clusters with different structures;

DESCRIPTION OF THE PREFERRED EMBODIMENTS

Figure 3:
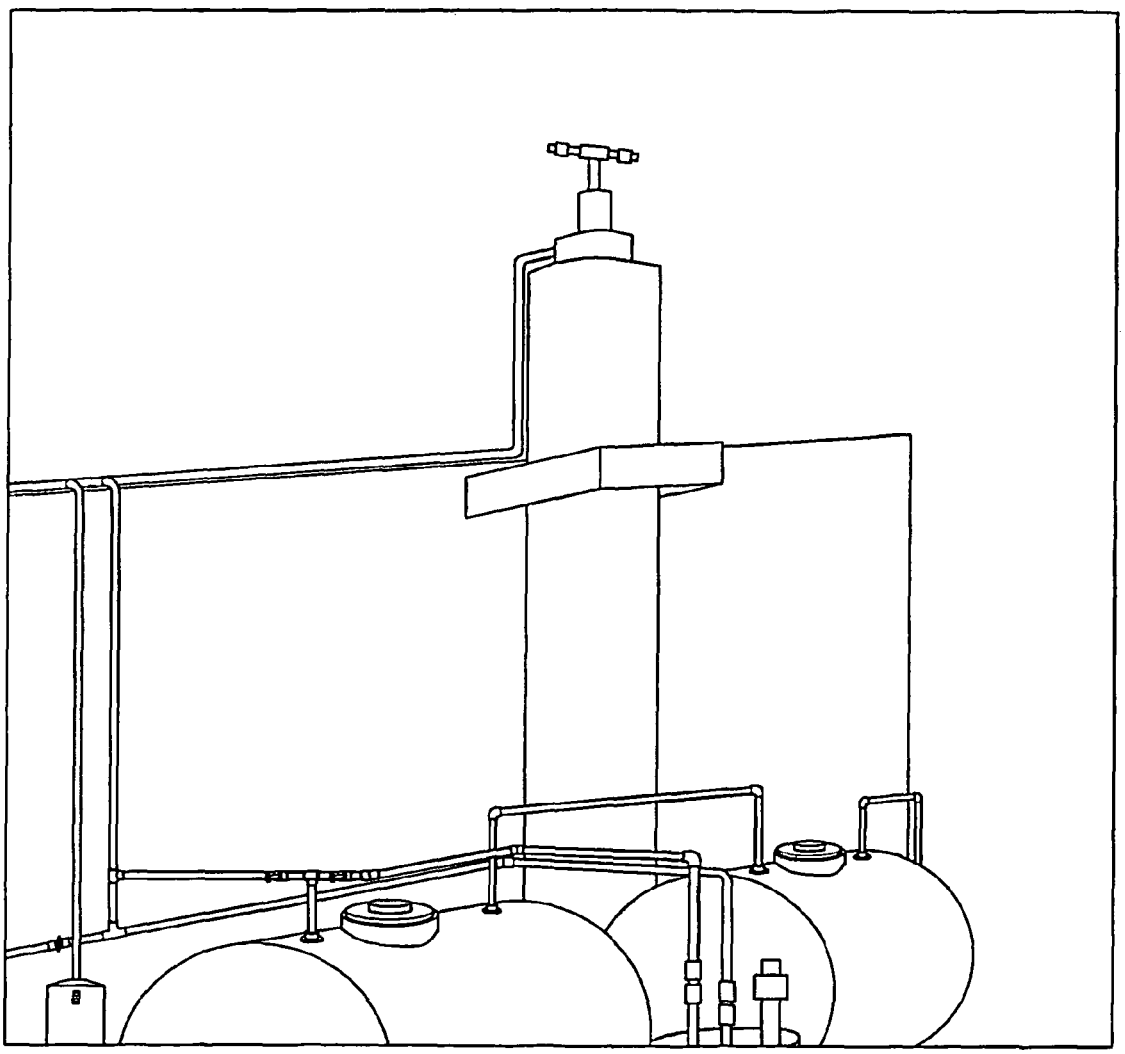
FIG. 3 is a view showing schematically a device for producing solid stable water clusters.

New methods for production of water clusters will be now described in detail.

It is known that ordinary water contains clusters which consist of water molecules. These variable water molecules are often called flickering-water-clusters because the hydrogen bonds are broken randomly by thermal energy and then recombine. The present invention deals with sold solid stable water clusters which are made of a fixed number of water molecules having a steady stable electric field surrounding them.

Solid stable water clusters can be created in accordance with the present invention by diluting soluble substances into ultra-pure water.

Such solid stable water/clusters range in size from tens of nanometers to a few microns in size. These have a permanent electric/dipole/moment. There is strong electric field surrounding them.

FIG. 1 shows an atomic force microscope picture tapping of one such sold solid stable water clusters where the electric field is explicitedly measured by its corresponding photo taken using the electric force mode of the same microscope. The sample consists of ultra-pure water containing many solid stable water clusters onto highly-ordered pyrolytic graphite. The atomic force microscope picture was taken by a tapping mode where physical contact is made on the first pass of the scanning device, but on the second pass the tip is held above the surface at a distance of 100 nanometers with a 1 volt bias is placed on the scanning tip, thus producing an electric force mode picture as in FIG. 2 as the tip then becomes effected by the electric field of the solid stable water clusters.

The largest solid stable water clusters are of micron size and are made from combinations of smaller solid stable water clusters that range in size from tens to hundreds of nanometers. One size distribution of these solid stable water clusters is shown here. In this ultra-pure water containing solid stable water clusters, the Lighthouse Model L-S60 Liquid Sampler is used to shown the clusters in the following distinct sizes: 0.1, 0.5, 0.2, 0.25, 0.3, 0.35, 0.4 and 0.5 Microns.

| Solid Stable Water Clusters Distribution | | | | | | | |
|---|---|---|---|---|---|---|---|
| 0.1 | 0.15 | 0.2 | 0.25 | 0.3 | 0.35 | 0.4 | 0.5 |
| 1179 | 2377.7 | 2208.7 | 1530 | 343.7 | 156.7 | 325 | 1173 |

Since the smallest solid stable water clusters are measured in nanometers, they are distinct from earlier emulsion products which were used before.

The strong electric fields surrounding these solid stable water clusters will increase the speed of chemical reactions, hence they can be used as catalysts.

It is well known that oil and water do not mix naturally by themselves. There are ways to bind oil with water as a stable product; either form an emulsion via ultra-sound or vigorous shaking or to add chemical binders, or a combination of both.

However, there is a practical problem of how to introduce these solid stable water clusters into combustion fuels which feed combustion engines of all types. It is necessary to break up the solid stable water clusters into their smaller components for the best catalytic effect. The nanotechnology emulsion method proposed here suspends nano-sized solid stable water clusters directly in all petroleum based fuels such as diesel, gasoline, jet fuel, etc. without adding additional chemicals such as binder and combustion enhancers.

Water/clusters have not been made part of petroleum fuels with a nano-emulsion requiring no more than 3 parts per million of sold stable water clusters waters.

FIG. 3 shows an actual production device. One tank is the supply, where diesel is placed. It is pumped through a vertical ultra-sound shaft into a treatment tank to create a nano-emulsion.

Thus an additive for fuel is a solution that contains solid stable water clusters made from water molecules. The solution is a special emulsion that contains a suspension of small water droplets of submicron size. The emulsion is created via vigorous shaking of water that contains sold stable water clusters and petroleum products such as diesel fuel, gasoline, and jet fuel using ultrasound device. The emulsion is added to the fuel of combustion engines and the like, gasoline, diesel, natural gas, etc., which combustion engines can be in trucks, cars, ships, airplanes, locomotives, or electricity generating plants.

A skin care product in accordance with the invention can include a solution that contains solid stable water clusters in accordance with the invention. The solution can be an emulsion that contains a suspension of small water droplets which contain the solid stable water clusters in other non-water-soluble liquids. The non-water-soluble liquids can be liquids selected from the group consisting of oil and a cream.

The skin care products described above can include additional chemicals. On the other hand in the skin care product in accordance with the invention no chemicals can be added. The emulsion for the skin products can be an emulsion generated via vigorous shaking of water that contains solid stable water clusters, and water droplets can be of submicron size.

The skin care products in accordance with the invention can include ingredients having health benefits. The ingredients can include vitamins, minerals, hormones, natural herbal extracts, etc.

A food product in accordance with the invention contains inventive solid stable water clusters. The solution can be an emulsion that contains a suspension of small droplets the solid stable water clusters in other non-water-soluble liquids. The food product can contain additional substances, or no substances can be added. The water droplets are submicron size. The above-mentioned emulsion can be generated via vigorous shaking of water that contains the solid stable water clusters.

Numerous food products can be produced with the use of the solid stable water clusters and corresponding food ingredients. Also drinking and non-drinking water can be produced such that it contains the inventive solid stable water clusters.

Solid stable water clusters can be produced by diluting organic and/or inorganic material with very pure water. It is necessary to dilute the inorganic materials to a certain dilution before it is possible for the stable water clusters to form. It is also necessary to use 18.2 MΩ*cm million ohms per centimeter quality water as the dilution water in order to have the largest amount of stable water clusters. Within the ultra-pure water industry, equipment is available to purify water to 18.2 MΩ*cm of resistance.

An additional criteria is used to ensure the highest possible quality. The Light House LS-60 laser particle counter allows an analysis of the number of particles per unit volume present. The proper use of containers is ensured thus controlling the leaching or contamination from other chemicals or particles which could be present in the containers themselves. The two types of containers that are used in the inventive method are composed of quartz and polypropylene or similar materials.

Distilled commercially available water has typical 50 thousand 0.1 micron particle or large counts per 1 ml samples. The inventive method uses ultra-pure water that has particle counts less than 500 particles per 1 ml above 0.1 micron. See Table 1 below as a comparison of commercially available distilled water and our ultra-pure-water.

The ultra-pure water is labeled "10-Water" and is the water that is used with the inventive method. Measurements are from 0.1 microns to 0.5 microns.

TABLE 1

Comparison of Commercially available distilled water to our ultra-pure "10 Water".

Distilled water
Location: 01  SAMPLE SIZE: 1  SYRINGE: 25
Data is CUMULATIVE and NORMALIZED

| Date | Time | 0.1 | 0.15 | 0.2 | 0.25 | 0.3 | 0.35 | 0.4 | 0.5 |
|---|---|---|---|---|---|---|---|---|---|
| Mar. 1, 2009 | 16:15:59 | 56180 | 18540 | 6760 | 3720 | 1620 | 1040 | 860 | 660 |
| Mar. 1, 2009 | 16:16:00 | 56220 | 18840 | 7280 | 4140 | 1660 | 1020 | 840 | 660 |
| Mar. 1, 2009 | 16:16:01 | 56780 | 18540 | 7060 | 4200 | 1880 | 1320 | 1060 | 860 |
| Run Results | | | | | | | | | |
| Mar. 1, 2009 | 16:16:01 | 56393 | 18640 | 7033.3 | 4020 | 1720 | 1126.7 | 920 | 726.27 |

"10 Water"
LOCATION: 01  SAMPLE SIZE: 1 ml  SYRINGE 25 ml  TARE: 0.2 ml
Data is CUMULATIVE and NORMALIZED

| Date | TIME | 0.1 | 0.15 | 0.2 | 0.25 | 0.3 | 0.35 | 0.4 | 0.5 |
|---|---|---|---|---|---|---|---|---|---|
| Mar. 1, 2009 | 16:02:05 | 20 | 0 | 0 | 0 | 0 | 0 | 0 | 0 |
| Mar. 1, 2009 | 16:02:06 | 20 | 0 | 0 | 0 | 0 | 0 | 0 | 0 |
| Mar. 1, 2009 | 16:02:07 | 20 | 0 | 0 | 0 | 0 | 0 | 0 | 0 |
| Run Results | | | | | | | | | |
| Mar. 1, 2009 | 16:02:07 | 20 | 0 | 0 | 0 | 0 | 0 | 0 | 0 |
| Run Complete OK | | | | | | | | | |

Therefore the first step of the inventive method is the production of "10-water" to use as the dilution water to create stable water clusters.

Next the process of dilution is carried out in an Argon gas filled chamber. It is important to carry out the entire procedure in an atmosphere free of carbon dioxide. Pure 18.2 Mohm water will degenerate rapidly to 1 Mohm water or less in a matter of seconds when it is exposed to normal atmosphere due to the presence of carbon dioxide. Such an exposure of ultra-pure water to CO2 will form carbonic acid thereby producing ions to conduct electricity.

Therefore, the dilution in accordance with the invention is carried out by adding a small amount of materials to the "10-water" in the Argon filled gas chamber. In the following example, sodium chloride is used:

In table 2 the particle size distribution of sodium chloride solution with concentration of 10 to the minus 3 Mole is shown.

TABLE 2

Ten to the minus 3 Dilution of NaCl made with "10 Water"

Location: 01  SAMPLE SIZE: 1 ml  SYRINGE: 25 ml
Data is CUMULATIVE and NORMALIZED

| Date | Time | 0.1 | 0.15 | 0.2 | 0.25 | 0.3 | 0.35 | 0.4 | 0.5 |
|---|---|---|---|---|---|---|---|---|---|
| Mar. 1, 2009 | 16:14:21 | 26880 | 10060 | 5740 | 4040 | 2600 | 2160 | 1840 | 1540 |
| Mar. 1, 2009 | 16:14:22 | 27340 | 9640 | 5820 | 4020 | 2800 | 2220 | 1840 | 1520 |
| Mar. 1, 2009 | 16:14:23 | 27140 | 9780 | 5660 | 4120 | 2900 | 2240 | 1860 | 1460 |
| Run Results | | | | | | | | | |
| Mar. 1, 2009 | 16:14:23 | 27120 | 9826.7 | 5740 | 4060 | 2766.7 | 2206.7 | 1840 | 1506.7 |
| Run Complete OK | | | | | | | | | |

In Table 2 the particle size distribution of sodium chloride solution is shown with concentration of 10 minus 3 Mole made from "10 Water". Dilution with "10 water" to 10 to the minus 7 under controlled non-atmosphere conditions equates to a linear downward diminishing of particles to a total of 2.7 total particles.

Notice should be made that when that same solution is diluted further to 10-7 M, particles of larger than 0.1 microns appear much more than the readings for 10-3. Since they cannot be ions, they can only come from the formation of water molecules into clusters that were detected.

| | | | | 1.7 times 10 to the minus 7 NaCl | | | | | |
|---|---|---|---|---|---|---|---|---|---|
| Location: 01 | | SAMPLE SIZE: 1 ml | | | SYRINGE: 25 ml | | TARE: 0.2 ml | | |
| Data is CUMULATIVE and NORMALIZED | | | | | | | | | |
| Date | Time | 0.1 | 0.15 | 0.2 | 0.25 | 0.3 | 0.35 | 0.4 | 0.5 |
| Mar. 1, 2009 | 16:09:27 | 3680 | 1020 | 340 | 120 | 20 | 20 | 20 | 20 |
| Mar. 1, 2009 | 16:09:28 | 3680 | 1200 | 440 | 300 | 100 | 40 | 40 | 40 |
| Mar. 1, 2009 | 16:09:29 | 3280 | 900 | 260 | 120 | 60 | 40 | 40 | 0 |
| Run Results | | | | | | | | | |
| Mar. 1, 2009 | 16:09:29 | 3546.7 | 1040 | 346.67 | 180 | 60 | 33.333 | 33.33 | 33.333 |
| Run Complete OK | | | | | | | | | |

Figure 4:
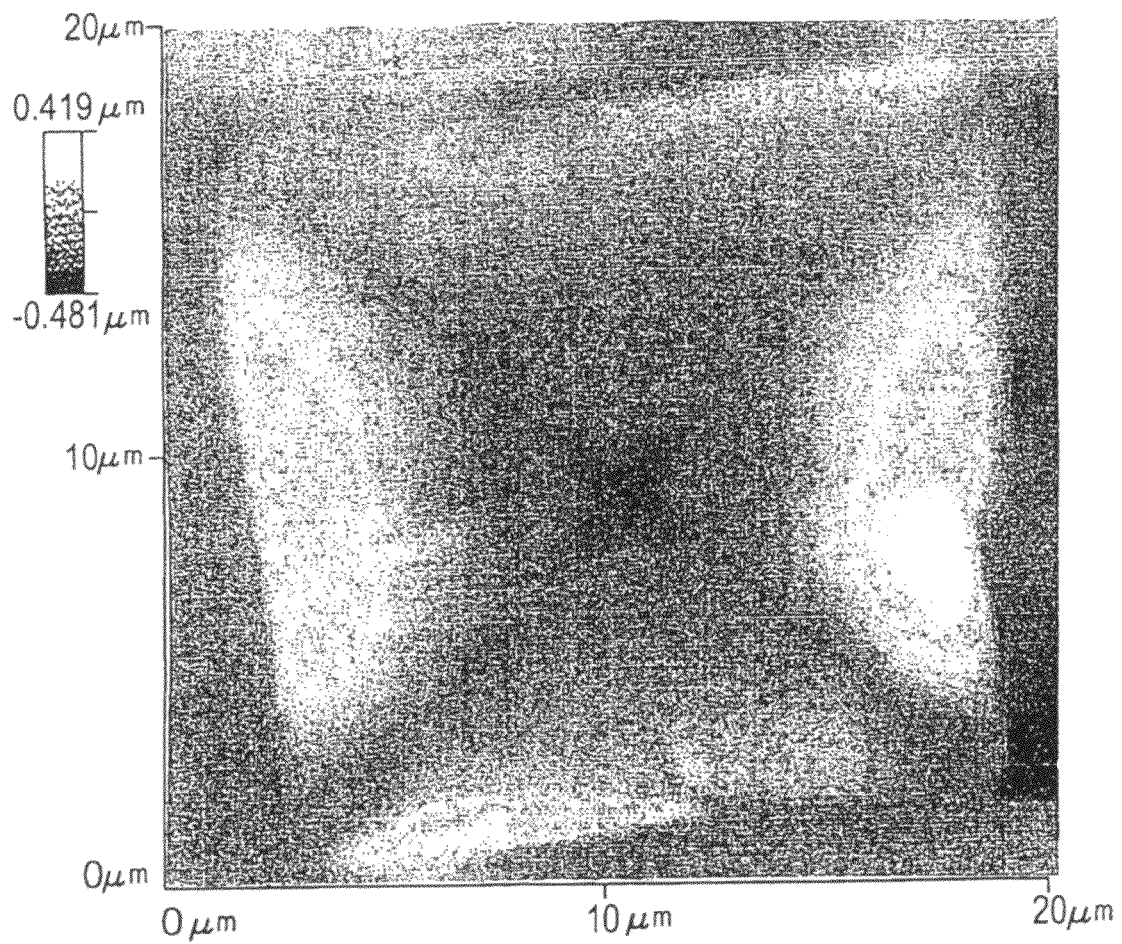
FIGS. 4-7 are atomic force microscope pictures of residues from dried sodium chloride solution for producing solid stable water clusters.

Atomic force microscope AFM pictures are taken and shown in FIG. 4 Tapping, Topo frw, NaCl crystal FIG. 4 shows pictures of residues from dried 10 times the minus 3 mole sodium chloride solution that show the crystalline form of sodium chloride FIG. 4 shows an atomic force microscope picture of the residue of Solution S after evaporation of liquid residue. The shape and size of stable water clusters in Solution S can be explicitly seen. Solution S is defined as the solution obtained by dilution of small amount of materials.

Figure 5:
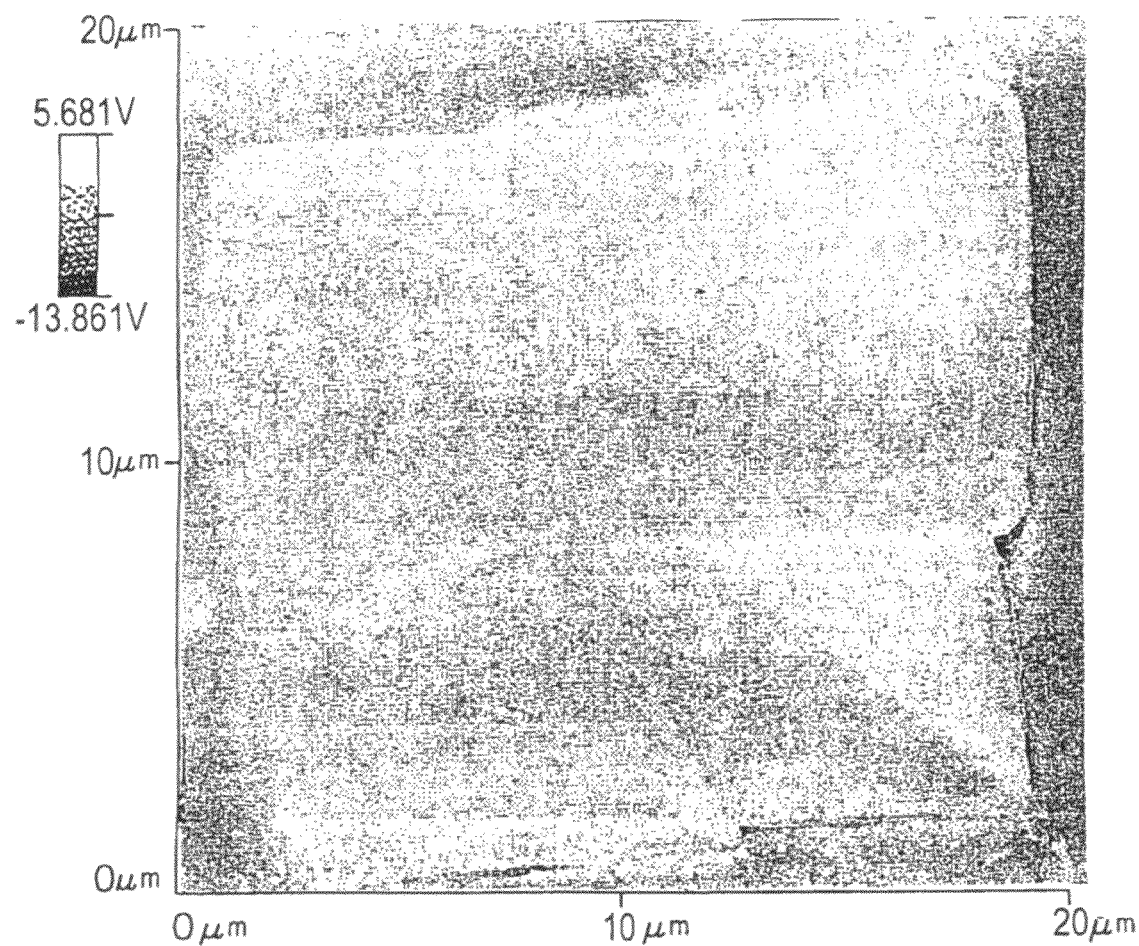

FIG. 5 Tapping Phase bkw EFM, NaCl crystal shows electric force microscope pictures of residues from dried 10 to the minus 3 Mole sodium chloride solution taken simultaneously with FIG. 4. The uniform color on the NaCl crystalline form indicates that there is no charge on the surface of the sodium chloride. At the right side of the picture the vertical edge indicates charge present from contamination on the microscope stage but no charge on the sodium chloride crystal.

Figure 6:
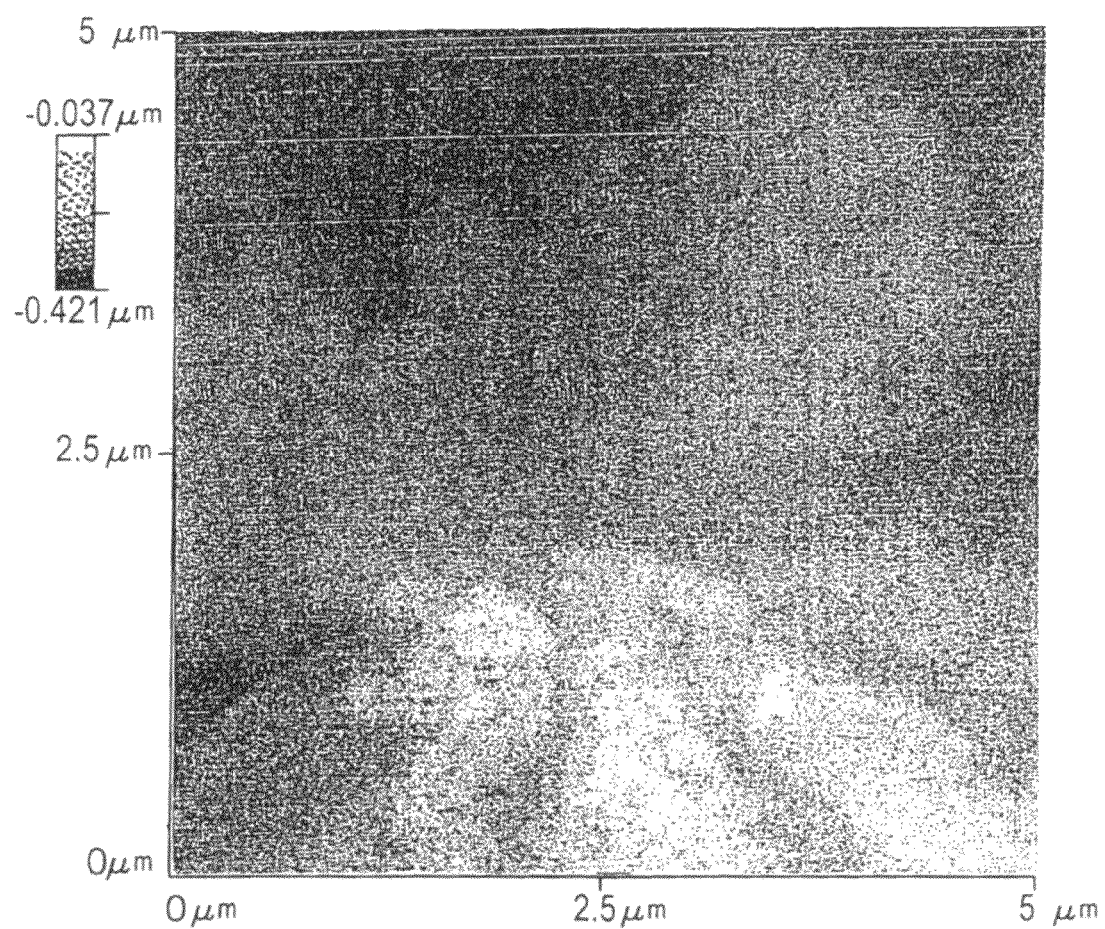

FIG. 6 Tapping Topo Frw, 1.7 e-7 diluent shows atomic force microscope pictures of residues from dried 1.7×10-7 M sodium chloride solution which illustrates the shape of stable water clusters and not the shape of the crystalline form of sodium chloride.

Figure 7:
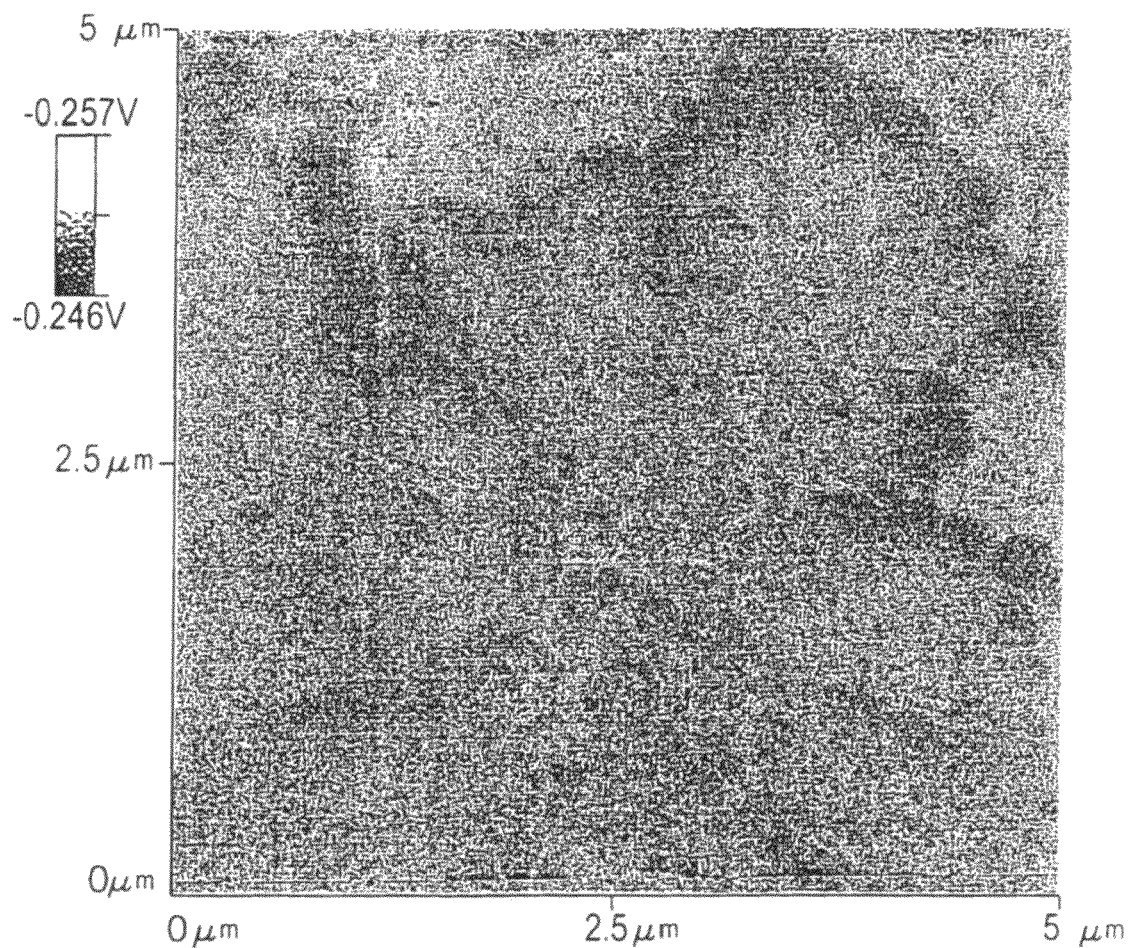

FIG. 7 Tapping Phase bkw, 1.7×e-7 diluent shows electric force microscope pictures of stable water clusters demonstrating that the crystalline structures are changed.

These water-clusters prepared with the above method from very dilute solutions are stable over a period of days, months, and years. The water clusters are especially stable.

The dilution process to make stable water clusters can be carried out in either small or large scale batches; a small scale batch can be done in liter or gallon containers whereas large scale batches can be done in containers for hundreds of gallons or more.

Figure 8:
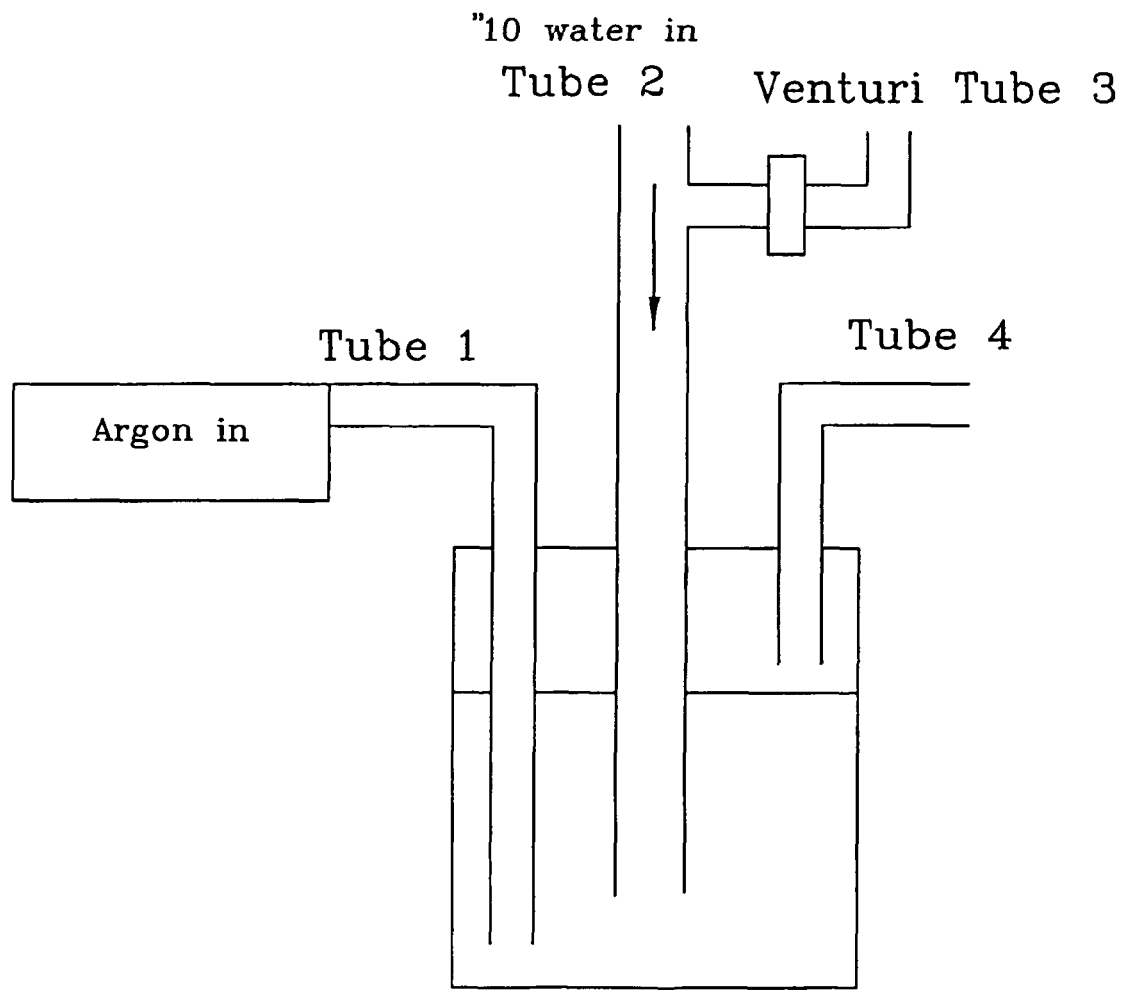
FIG. 8 is a view showing schematically a device for a small scale production of solid stable water clusters.

Small scale production is shown in FIG. 8, for the production of stable water clusters in a gallon container. The container, tubes, stoppers, etc., are made of polypropylene to minimize leaching problem that produces contamination of the product. The stopper on the top of the container has three holes for three tubes. The tube 1 allow argon to flow in, the tube 4 allows argon to flow out, allowing a positive argon gas pressure relative to normal atmosphere so that no air can flow in to contact the solution. This prevents the carbon dioxide contamination to the pure 10-water, or the final production solution.

The device can be scaled upward for mass production and can be automated for continual service.

The process takes place in the following manner:

Argon comes in from the Tube 1 and pushes all atmosphere within the bottle out through the Tube 4, "10 Water" is injected from the tube 2 in the middle into the bottle that is devoid of atmosphere and filled with Argon;

As "10-Water" enters the bottle, a tiny amount of Substance A is sucked into the bottle by Venturi effect at Ventur Tube 3, thereby allowing the dilution of Substance A to occur in an environment where no carbon dioxide is present and "10 Water" can maintain its purity.

Thus this production process of creation of stable water clusters includes adding a small amount of Material A in water, the purity of which is characterized by a resistivity of 18.2 Mohm and very small number of impurities, as measured by laser particle counter. The dilution process is carried out in carbon dioxide free atmosphere. The dilution process can be carried out in the presence of an inert gas, such as argon gas. The dilution process can be carried out in a bottle that is filled with argon gas and maintained at positive pressure so that no atmosphere will leak in. All the containers are leak and leach free vessels allowing no impurity/contaminants of any kind to contaminate the pure water or the very dilute solution where stable water clusters are created. The containers contain three outlet tubes on the top: one tube that argon flows in, one tube that argon flows out, and the third tube for pure water to add to the container. The third tube where pure water flows can suck in a small amount of dilute solute by Venturi effect. The dilution process is carried out without contact with normal air. The containers, tubes, stoppers, etc., are made of polypropylene or quartz or similar materials which prohibit contamination. The materials A can be any organic, or inorganic materials artificially created or found, or isolated from plants, animals, and humans, such as vitamins, amino acids, hormones, proteins, enzymes, polypeptides, polysaccharide, DNA, RNA etc. The solution from dilution can be used to enhance combustion for fuel, to improve health to enhance biochemical reactions, in industrial catalytic processes of all kinds, for the enhancement of textiles, to enhance electroplating and similar processes.

The production of stable water clusters in large scale by dilution of materials into very pure water was described above. It is often desirable to have a more concentrated solution with a much larger number of stable water clusters that normally obtainable through dilution of a single material into very pure water. In accordance with the invention it is proposed to enhance the production of stable water clusters to increase the number of clusters per unit volume.

It starts with a very dilute "Solution S" of some material A. As an example sodium chloride is used as material A. Material A is diluted with very pure water to a concentration of 1.7 times $10^{-7}$ mole prepared under strict conditions as discussed above. The number of stable water clusters in the Solution S can be measured by a laser particle counter such as a Lighthouse Liquid Particle Counter LS-60 and those results are shown in Table 3.

| 1.7 times 10 to the minus 7 NaCl | | | | | | | | | |
|---|---|---|---|---|---|---|---|---|---|
| LOCATION: 01 DATA is CUMULATIVE | | SAMPLE SIZE: 1 ml | | SYRINGE 25 ml | | | TARE: 0.2 ml | | |
| DATE | TIME | 0.1 | 0.15 | 0.2 | 025 | 0.3 | 0.35 | 0.4 | 0.5 |
| Mar. 1, 2009 | 16:09:27 | 3680 | 1020 | 340 | 120 | 20 | 20 | 20 | 20 |
| Mar. 1, 2009 | 16:09:28 | 3680 | 1200 | 440 | 300 | 100 | 40 | 40 | 40 |
| Mar. 1, 2009 Run Results | 16:09:29 | 3280 | 900 | 260 | 120 | 60 | 40 | 40 | 40 |
| Mar. 1, 2009 Run Complete OK | 16:09:29 | 3547 | 1040 | 346:7 | 180 | 60 | 33.3 | 33.3 | 33.3 |

Table 3 shows particle counts of various sizes from 0.1 micron to 0.5 microns from a very dilute sodium chloride Solution S of concentration $1.1 \times 10^{-7}$ mole prior to concentration method discussed below.

Figure 9:
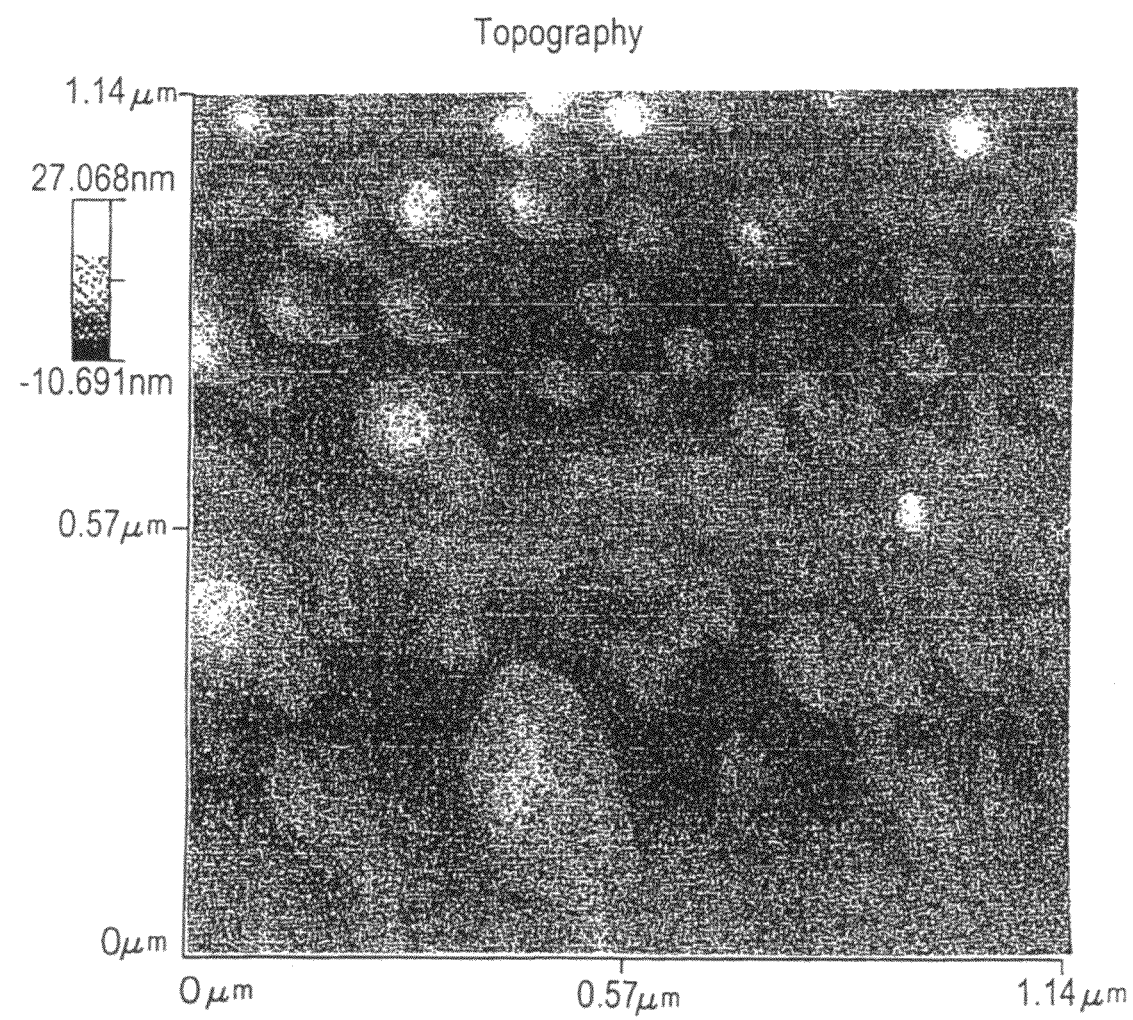
FIGS. 9 and 10 are atomic force microscope pictures of residues of another embodiment for producing solid stable water clusters.

FIG. 9 shows an atomic force microscope picture of the residue of Solution S after evaporation of liquid residue. The shape and size of stable water clusters in Solution S can be explicitly seen.

created by material A will grow larger. The result will be a solution higher in concentration of stable water clusters per given volume.

Table 4 presents the distribution of the sizes of stable water clusters as counted by laser particle counter for Solution S' with the addition of Material B using the method herein described. An increase of stable-water-cluster per given volume is shown:

| Enhanced Solution S with Material B | | | | | | | | | |
|---|---|---|---|---|---|---|---|---|---|
| Location: 01 Data is CUMULATIVE and NORMALIZED | | SAMPLE SIZE: 1 ml | | SYRINGE: 25 ml | | | TARE: 0.2 ml | | |
| Date | Time | 0.1 | 0.15 | 0.2 | 0.25 | 0.3 | 0.35 | 0.4 | 0.5 |
| Mar. 1, 2009 | 16:29:08 | 163260 | 147920 | 112620 | 81360 | 44100 | 31800 | 26460 | 20500 |
| Mar. 1, 2009 | 16:29:09 | 163720 | 148300 | 113780 | 81080 | 2880 | 31060 | 25640 | 20120 |
| Mar. 1, 2009 Run Results | 16:29:10 | 161900 | 147867 | 112560 | 80713 | 43293 | 31467 | 26200 | 20420 |
| Mar. 1, 2009 Run Complete OK | 16:29:10 | 162960 | 147867 | 112560 | 80713 | 43293 | 31467 | 26200 | 20420 |

The number of stable water clusters can be increased in the very dilute Solution S by adding a second material that has a permanent electric dipole moment. Using small droplets of the second material designated as Material B, the material B has been diluted below $1.0 \times 10^2$ mole; Material B is then added to Solution S in small droplets.

Material B could be vitamin E or omega 3 oil, or any other organic or inorganic material or the mixture of many different kinds of materials. As a specific example, omega 3 oil is used as Material B.

A very small amount of omega 3 oil is used and mixed with very pure water, preferably under surrounding argon gas. Since oil and water do not mix, additional processing is needed to mix oil and water. For thorough mixing ultrasound vibration is used so as Material B will be pulverized into a colloidal suspension. For maximum effect the oil molecule must be in contact with water molecules directly. Oil will not go into solution with water but rather together they form an emulsion. Then a small amount of this thoroughly mixed emulsion of Material B and pure water is added into Solution S. The final Solution S' should have a minute concentration of Material B in the range of $1.0 \times 10^{-7}$ mole.

The surface of the new organic molecule (omega 3 oil) will have many positively and negatively charged spots. Surrounding water molecules and stable water clusters will attach to these charged spots and these charged spots will provide growth sites for the stable water clusters. New stable water clusters will grow and existing stable water clusters Table 4: shows particle counts of various sized stable water clusters from 0.1 microns to larger than 0.5 microns from Solution S' after performing the enhancing discussed herein.

Figure 10:
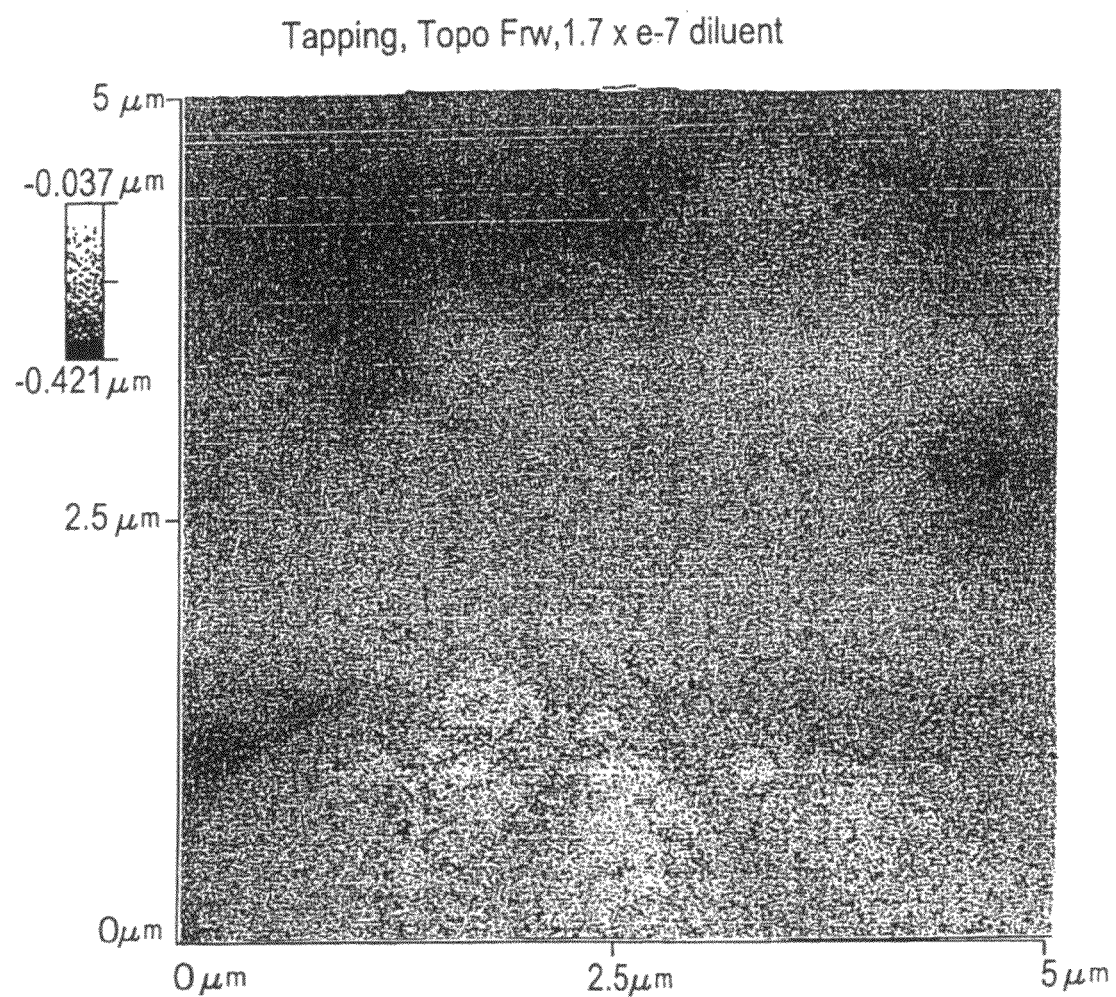

FIG. 10 shows the pictures from atomic force microscope of the residues obtained from dehydrated Solution S' after process of enhancement is complete (Tapping, Topo Frw, 1.7×3-7 diluent). The size and distribution of stable water molecules are explicitly displayed.

Thus in this method an enhanced Solution S' is produced from an existing Solution S, which is known to have stable water clusters by adding small amount of a second Material B to Solution S, whereas the Solution S' will increase in the number of stable water clusters. The material B is liquid phase, which may be inorganic or organic. It can be is one of the petroleum products, diesel, gasoline, or its derivatives. The Material B is first thoroughly mixed with very pure water by vigorous shaking such as ultrasound shaking to form a uniform mixture, which is an emulsion. A small amount of the uniform mixture is added to very pure water under the argon gas. The very pure water comes from a water producing machine that produces water with very high purity as measured by resistivity meter to be close to 18 Mohm-cm. Each step of production process and not any part of the solution is ever exposed to carbon dioxide in the air. All the containers, tubes, stoppers, joints are made of materials, which do not leak or leach when in contact with very pure water. Examples of such materials are quartz and polypropylene. The enhanced Solution S' of stable-water-molecules can be used to be a fuel catalyst in combustible fuel such as gasoline, diesel, natural gas, jet fuel, heavy oil, and coal, to reduce coking in processing plants in oil refineries, power plants, manufacturing facilities that produces petroleum derived products, for health purposes such as supplements, medicines, or energized homeopathic remedies, in industrial processes such as the manufacture of nitrogen fertilizer. In industrial processes which require the use of water to enhance or suppress the enzymatic effect on bioactivities such as fermentation, to change or strengthen textiles, to improve the function and life of acid lead batteries.

In accordance with a further embodiment of the invention the following device can be used for industrial large-scale production of products containing a catalyst made from stable water clusters.

Figure 11:
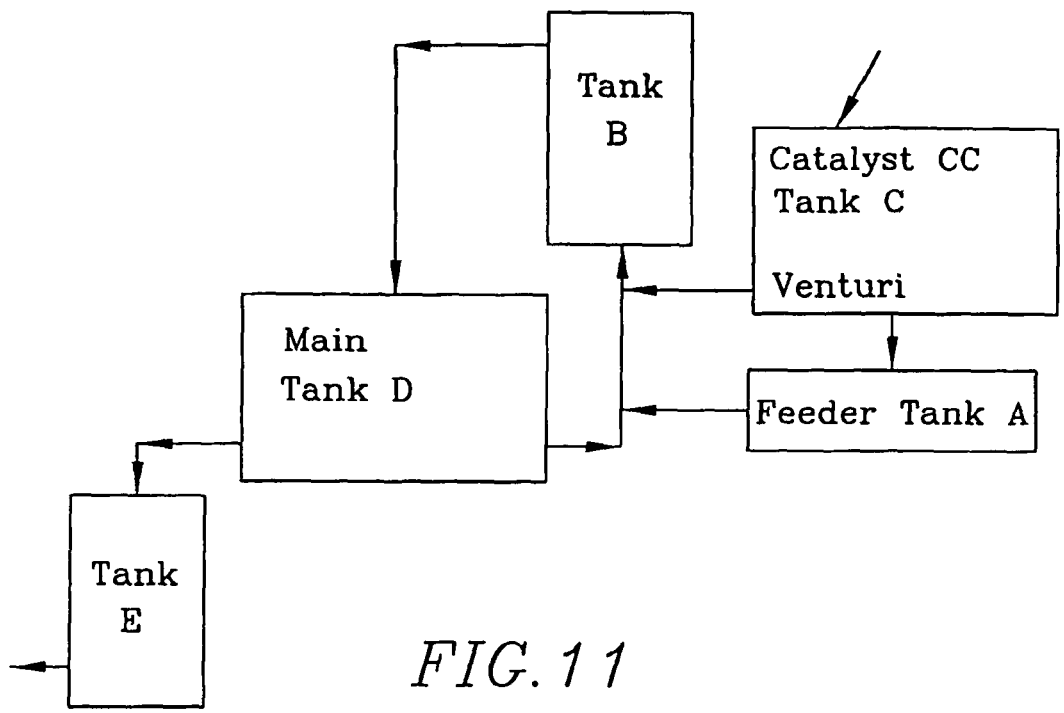
FIGS. 11 and 12 are views schematically showing processing of petroleum fuel to be mixed with a catalyst based on solid stable water clusters.

FIG. 11 shows the device that includes a feeder tank A on the right with diesel fuel. The diesel fuel is pumped to tank B, where an ultrasound vibration device is installed. Before the fuel reaches tank B, a small amount of concentrate catalyst CC is extracted from tank C by Venturi effect. The ratio R of c concentrate catalyst CC to diesel fuel is set to be very small, such as 1 part CC to 1000 part diesel. The concentrated catalyst CC is mixed thoroughly with diesel fuel in tank B by ultrasound vibration. The flow rate in and out of tank B is controlled to ensure a given amount of ultrasound vibration mixing time to achieve a thorough mixing of CC with the diesel. The mixture of CC plus diesel fuel flows out of tank B and reaches the main tank D. Usually the mixing requires more than one pass through tank B. Then a second round of mixing is achieved by pumping continuously the mixture of diesel and CC form the main tank D back through bank B, for further ultrasound vibration mixing, then back to main tank D.

When the mixing is satisfactorily completed and the diesel fuel is considered to have the necessary catalyst added, it is ready to go to the storage tank E for shipping and distribution to users of diesel fuel. Similar procedure can be applied to gasoline, jet fuel, kerosene or other liquid petroleum products.

Figure 12:
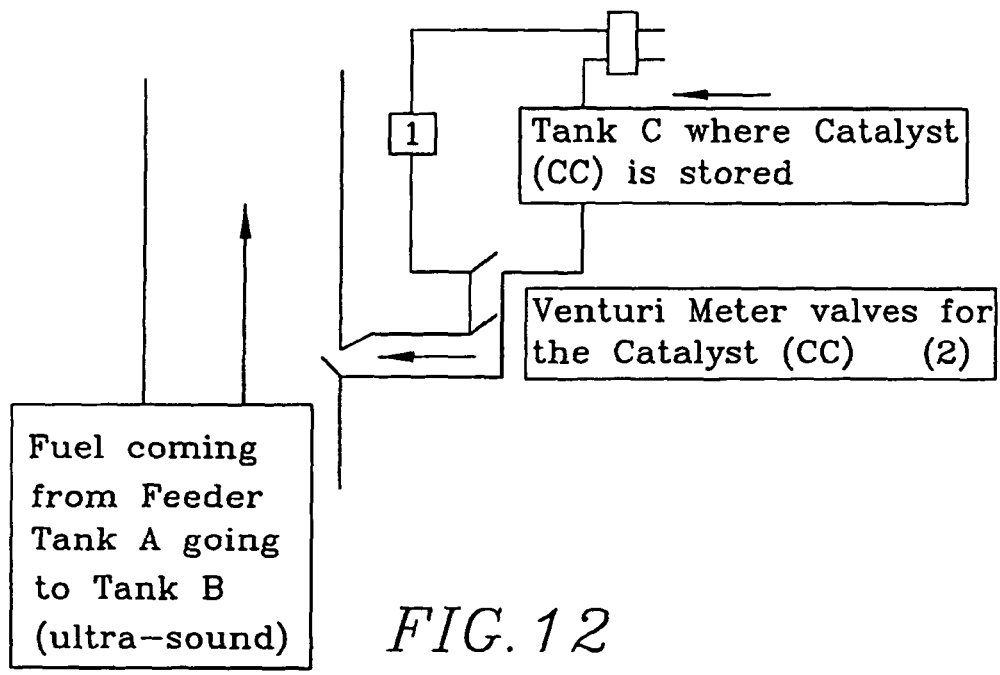

While FIG. 11 shows a flow diagram for processing large quantity of petroleum fuel to be mixed with a liquid catalyst without chemical binder, FIG. 12 shows a flow diagram of the addition of concentrate catalyst CC from Tank C through Venturi to Tank B.

Concentrate catalyst CC enters from tank C. Venturi meter valves allows CC to enter into tube carrying fuel toward tank B ultra-sound. Meter tube measures the volume $V_1$ of CC to be mixed with diesel of volume $V_2$. The volume of diesel $V_2$ is controlled by a valve coming from the feeder tank A. The ratio $R=V_1/V_2$ is fixed. One way valve allows CC to go into the tube by Venturi effect to mix with diesel coming out from tank A into tank B. Diesel coming out from tank A to flow into ultrasound tank B.

In summary the procedure for producing large quantities of catalyst CC for processed fuel by mixing vigorously a small amount of concentrate catalyst CC with diesel or like petroleum based fuels can be expressed as a formula:

$$CC+D=CD$$

where the ratio R is defined by the amount of CC to D by R=CC/D. As an example the ratio is chosen to be 1/1000 in one case.

The method and equipment disclosed can be used generally with any concentration of CC. CC would contain a significant amount of stable water clusters to be mixed with any solution D, such as diesel, gasoline, oil, alcoholic products or the like or to make hand cream, face cream or any health product.

To have a maximum effect of mixing and to ensure the purity of the product produced, the entire system from tank A to tank B, C, D and E would be maintained under a positive pressure of argon gas so as to eliminate the contamination from carbon dioxide and oxygen that would be present in normal room atmosphere.

Some specific examples are presented below for producing a large amount of dilute liquid CD which contains a lower density of stable water clusters from mixing concentrate CC with liquid D.

D is diesel fuel, and CD is a fuel additive to be added to diesel fuel to enhance combustion and reduce pollution.

D is gasoline, and CD is a fuel additive to be added to gasoline to enhance combustion and reducing pollution.

D is any fuel, such as jet fuel, or kerosene, and CD is the fuel additive for jet fuel and kerosene.

D is oil, and CD is oil with stable water clusters that can be used for hands, face, etc., for the enhancement of look and health.

D is pure water, and CD is water with small amount of stable water clusters the can be used for health purpose.

D is wine and CD is wine with a small amount of stable water clusters that can be used as higher quality wine.

Summarizing this embodiment it should be mentioned that the thusly produced large quantities of CD could be a catalyst or oil, or cream, produced by mixing vigorously a small amount of concentrate CC which contains a high density of Stable water clusters with a solution D which can be diesel, gasoline, oil, water or cream to form a dilute solution CD which could be a catalyst for diesel, gasoline or other petroleum fuel or cream. The mixing is done by ultrasound, the mixing ratio R of CC to D can be set to be a small amount, such as 1/1000, the ratio can be maintained by two automatically controlled valves, where the first valve controls the amount of D from feeder tank A, the second valve controls the amount of CC entering into the meter region, where CC is mixed with D by Venturi effect. The mixed and dilute liquid CD is pumped from the said ultrasound tank into the main tank, the mixed CD in the main tank is pumped to go through the ultrasound tank continuously for a short duration so that the mixture CD is thoroughly mixed and stays in the main tank. The thoroughly mixed liquid CD enters into a storage tank E, ready for shipment.

The thoroughly mixed liquid CD can be used as fuel additive, whereas the fuel D can be diesel, gasoline, kerosene, jet fuel, etc.; as health purpose, whereas the said D is oil, and CD can be some emulsion or liquid form for health purpose such as for hands, face, etc.; as an alcoholic beverage whereas D can be any alcoholic beverage, such as wine, beer, etc.; the liquid D can be pure water, and CC is concentrate for some special stable water clusters C, whereas the end product CD is for health uses, such as drinking.

The solid stable water clusters produced in accordance with the present invention have specific molecular structures.

Figure 14:
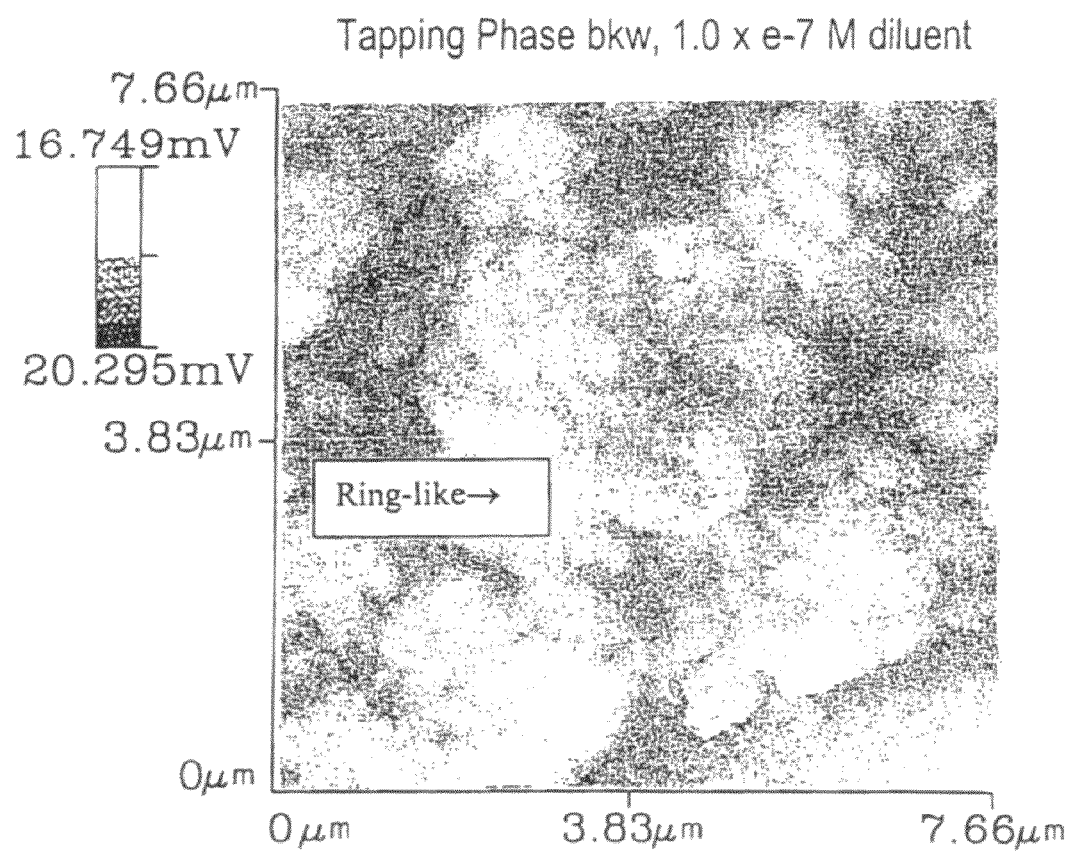

As explained above, it is possible to create stable water clusters by dilution. The dilution of sodium chloride is used as an example. The dilution of both organic and inorganic materials in ultra pure water will produce stable water clusters. The existence of stable water clusters is revealed by letting stable water clusters water or referred to as cluster water evaporate on a glass slide and then examining the residue left. This is done by light microscope and atomic force microscope. FIG. 14 shows one of the solid stable water clusters. There are various shapes of stable water clusters. Some of them look like cotton balls. In FIG. 14 several ring-like structures can be seen, which can be considered to be more fundamental.

In FIG. 14 the dimensions of the photo are 7.67 micron× 7.67 microns. The ring-like structure shown in the picture is approximately 1 micron size.

Figure 13:
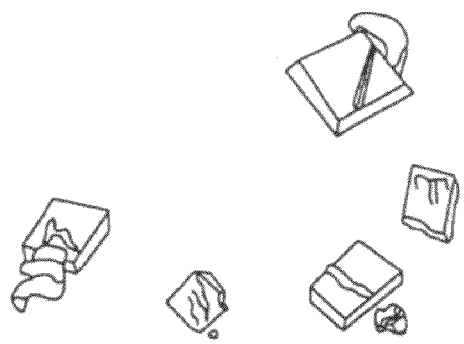
FIG. 13 is a view showing microscope pictures of sodium chloride crystals.

In solid state physics, when the phenomena of phase transition is considered, an important principle is scaling. The interaction is energy, which is called the Hamiltonian in its operator formalism, scales. That is, the same kind of interaction occurs, no matter what the size of the object. FIG. 13 shows the shape of sodium chloride in various sizes shown in microscope with a magnification of 400×.

The two left-most clusters of sodium chloride crystals can be noticed. The face-centered cubic structure of sodium chloride shows itself as a square shape in the illustrated two dimensional pictures. The smallest to the largest square shaped sodium chloride cubic structure spans a factor of approximately 100. The face-centered cubic structure of sodium chloride remains even down to nanometer size. In comparison, the scaling of the ring-like structure will likewise go down to nanometer size.

There are occasions when the ring-like structure is not complete, but is only half complete. Then kidney-like structures are formed as shown in FIG. 15. In FIG. 15 picture the dimension is 1.66 micron×1.66 microns. Kidney-like structure is approximately 600 nm to 700 nm.

When the residue from evaporated cluster water is examined with atomic force microscope at size below one microns, some more precise pictures can be seen. One of such pictures is shown in FIG. 16. There are pentagons, with five side, hexagons with six sides, rectangle with four side. A group of pentagons and hexagons sometime form into soccer-ball-like structure. In FIG. 16 the picture dimension is 0.63 micron× 0.63 microns. Many four, five and six sided ring structures can be seen. These structures range from approximately 30 nm to 50 nm in size. These structures combine to form soccer-ball-like patterns.

Figure 17:
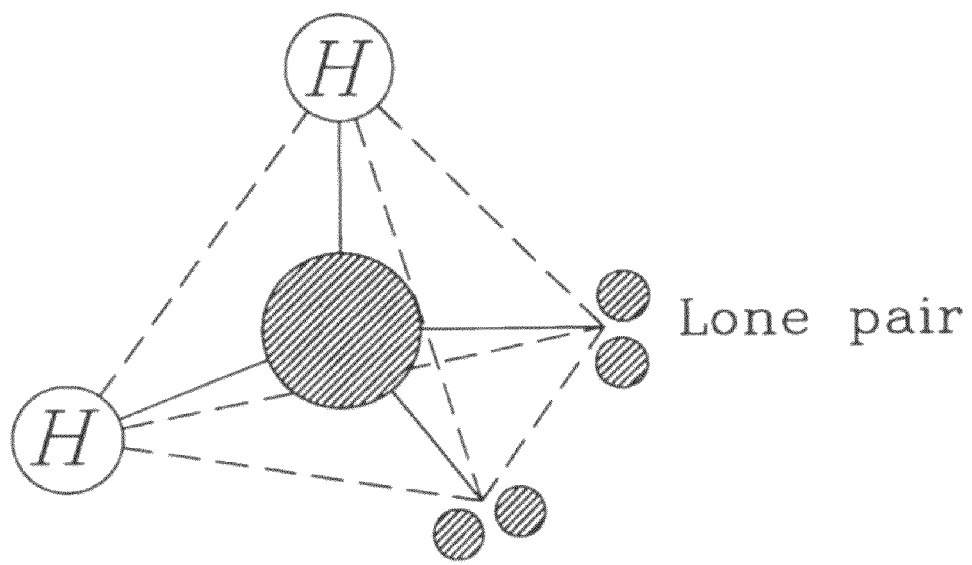
FIGS. 17-20 are views showing various shapes of solid stable water clusters.

The lone pair shown in FIG. 17, where water molecule is composed of two hydrogen atoms and one oxygen atom. These three atoms occupy the vertex of a tetrahedron.

Figure 18:
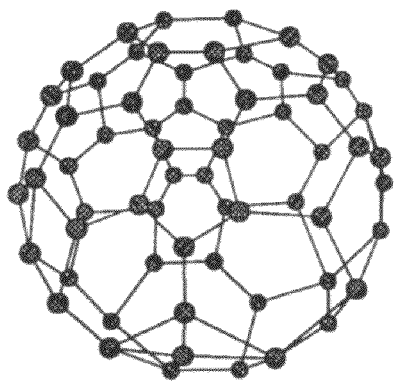

When many water molecules combine together to form a cluster, it is equivalent to hooking many tetrahedrons together. The lowest energy states for water clusters seem to point to pentagon and hexagon configurations, with oxygen molecules occupying the vertices of the pentagons, hexagons, and sometimes rectangles. By doing so, these pentagons and hexagons will form a soccer-ball-like configuration, as shown in FIG. 18. Mathematically they can be presented by:

$$5^n 6^m$$

where n and m indicate the number of pentagons and hexagons that constitutes a soccer-ball-like configuration. For the smaller soccer-ball-like configuration, the vertex, where two lines meet, is the site of the oxygen atom. The hydrogen atoms are spread along the line joining the vertices. In general it may have four side polygons, and it may not even have a closed cage structure like a soccer ball. It is simply the various combination of pentagons, hexagons, and four side polygons. It is represented by:

$$5^n 6^m 4^k,$$

where there are additional k number of four side rectangles. Furthermore, these are only units that can be constructed into the linear shape, helix shape, etc.

Figure 19:
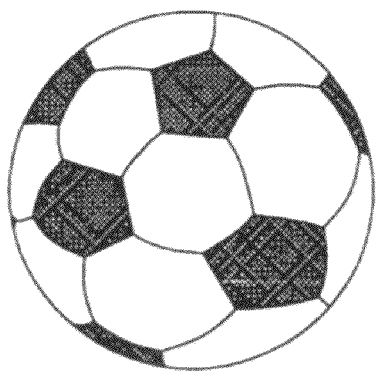

FIG. 18 shows balls with sixty vertices, while FIG. 19 shows a soccer ball with 20 hexagons white patches and 12 pentagons black patches, which can be denoted as $5^{12} 6^{20}$.

Figure 20:
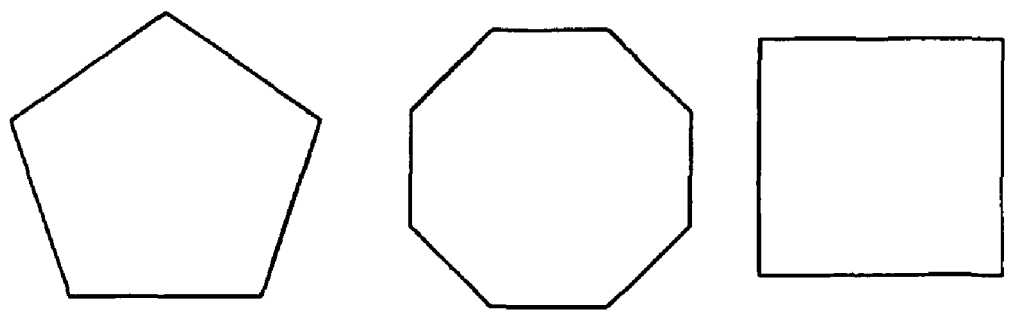

The most elementary ring structures are represented by the five-sided pentagon, six-sided hexagon, and four-sided rectangle, as shown in FIG. 20. The smallest molecular ring structures are composed of individual oxygen atoms occupying the vertices of these polygons and individual hydrogen atoms spreading along the lines joining these vertices.

FIG. 20 shows the symbolic ring structures of stable water clusters: from left to right; the pentagon; the hexagon; and the rectangle.

Thus the stable water clusters of the present invention are stable under normal room temperature and atmospheric pressure, with ring-structures ranging from microns, hundreds of nanometers, tens of nanometers. These ring-structures could be five-sided pentagons, six-sided hexagons four-sided rectangles. The smallest of these ring structures: five-sided pentagons, six-sided hexagons and four-sided rectangles are made up of individual oxygen and hydrogen atoms, the oxygen atom being at the vertex and the hydrogens atoms spreading along the lines joining the vertices. These pentagons, hexagons or rectangles may join together to form larger structures, which are part of stable water clusters. The larger structures may be soccer-ball-like with n side being pentagons, m side being hexagons, and k side being rectangles, denoted by the formula: $5^n 6^m 4^k$, where n, k, m can be 0, 1, 2, 3, . . . to a very large integers. The larger structures, which may or may not include soccer-ball-like structures, may join together to form much larger stable water clusters, which are of linear shape, ring shape, kidney shape, or helix shape.

It is well known that the fundamental structure of genetic material, DNA, is a double-helix. The structure of DNA is extremely complicated due to the extent of its evolutionary development, building slowly for eons as a coded record of successful life decisions. There was a beginning point on this long evolutionary chain, a starting point prior to the appearance of DNA as found in more evolutionary chain, a starting point prior to the appearance of DNA as found in more advanced biological life forms and the beginning point would have been present in primitive single-cell organisms. To date, no one has isolated the mechanism for its formation. Although it is common knowledge that life comes from water and without water there is no life, no one has asserted that there is a direct link between water and the complex form such as DNA.

In accordance with the present invention the stable water clusters can have a helix structure, in particular, two helix twins together forming a double-helix similar to the DNA structure.

Figure 21:
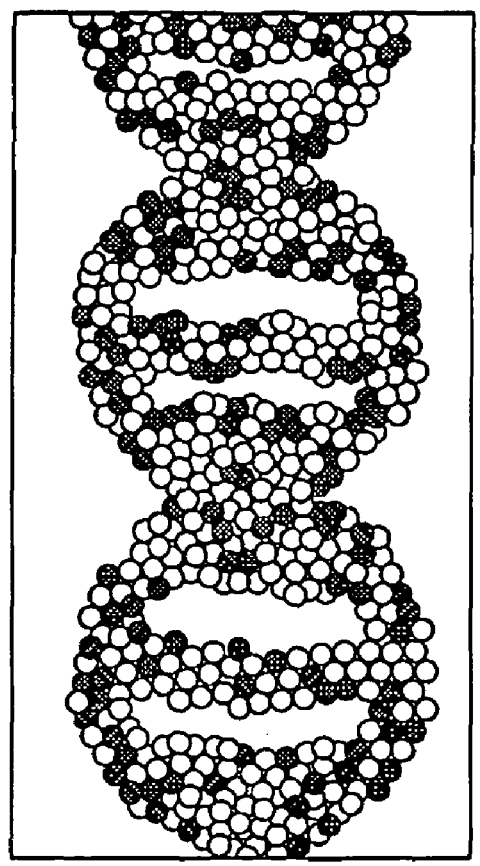
FIG. 21 is a view showing a picture of DNA with a double-helix structure.
Figure 22:
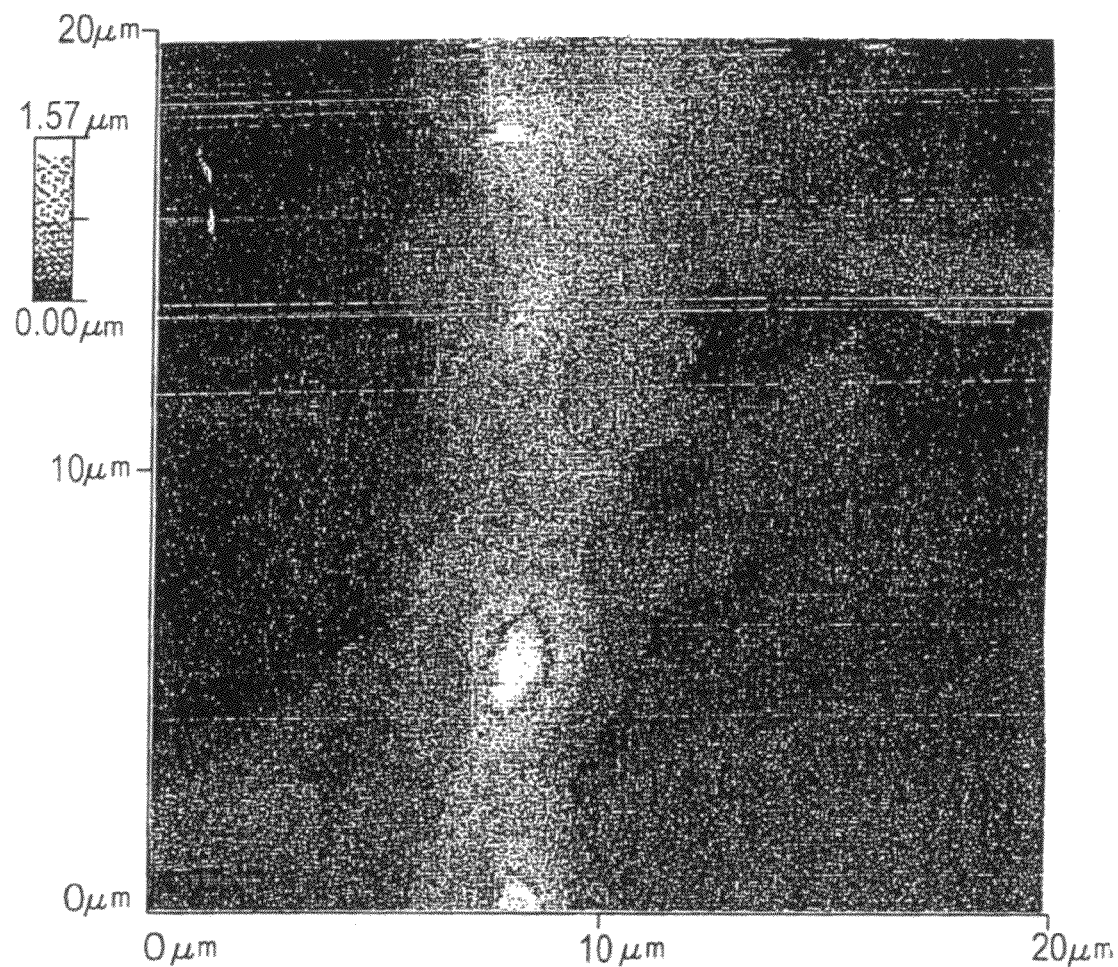
FIGS. 22-23 are atomic force microscope pictures of solid stable water clusters in a double-helix structure.
Figure 23:
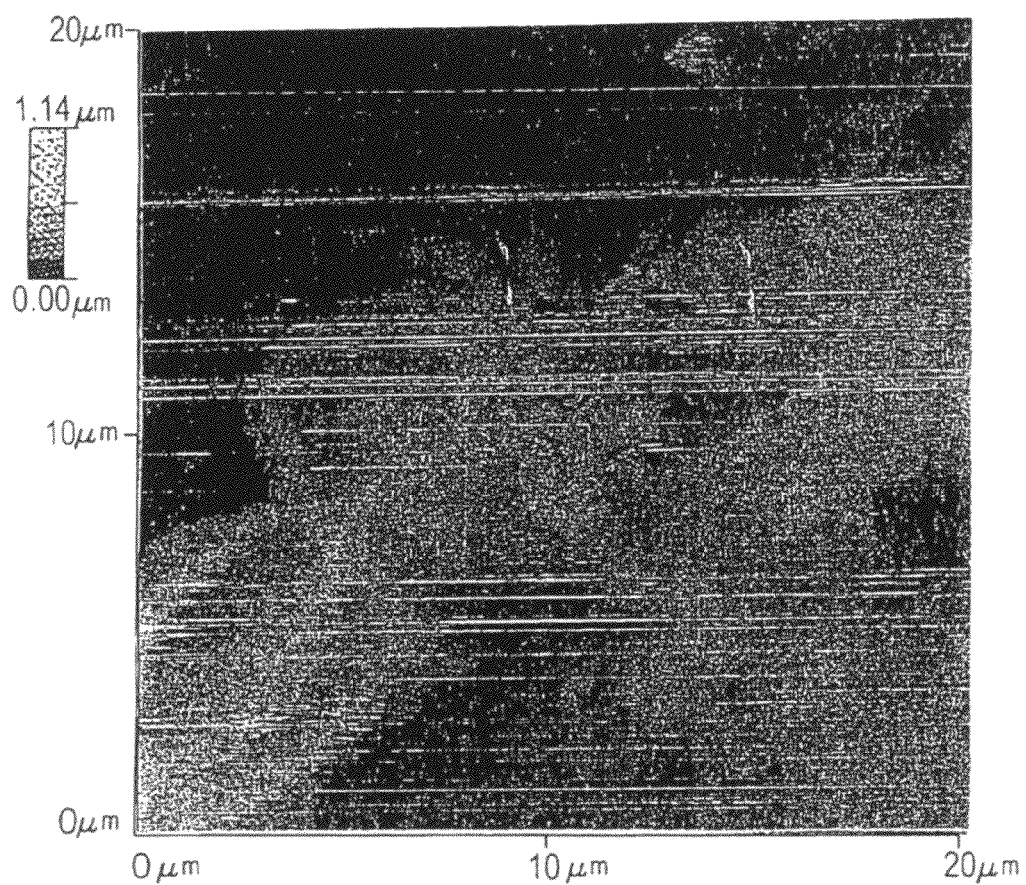

FIG. 21 shows the picture of a DNA with a double-helix structure. FIGS. 22 and 23 show two atomic force microscope pictures of the stable water clusters in accordance with the present invention in a double-helix structure.

If one compares FIG. 21 and FIGS. 22-23, there are differences and similarities. The difference is that the DNA double-helix is made up of four bases G, A, T, C whereas the stable water clusters double-helix is made from water molecules.

The similarity is that they are both double-helixes, a scaled image of each other. The width of the stable water clusters double-helix is approximately 2 microns, whereas the width of the DNA double-helix is approximately 2 nanometers, a factor of one-thousand-times smaller. By scaling DNA molecules one-thousand-times they look similar to the double-helix stable water clusters.

It is expected that the double-helix structure of stable water clusters can occur in nanometer, micron and even larger sizes.

The principle of scaling symmetry is shown. The Hamiltonian (a mathematical function, equal for many such systems to the sum of the kinetic and potential energies) of a crystal remains the same, independent of its scale. That means, no matter whether the scale is nanometer, micrometer or millimeter the Hamiltonian (energy) remains the same. Since the shape of the crystal is determined by the lowest energy state, then the shape of the crystal is the same independent of the scale (in physical terms, no matter the size of the crystal, nanometer, micrometer, or millimeter, the crystal retains the same shape). When one examines a salt (NaCl) crystal it has a cubic shape in millimeters (this can be seen using a simple magnifying glass). When observe a NaCl crystal is observed with an atomic force microscope, it is also a cubic structure even if in micron size. The same size of NaCl also persists to nanometer size, which is called face-centered cube.

Therefore, it is expected that the double-helix shape of stable water clusters in accordance with the present invention to remain regardless of micron or nanometer size.

A solution that contains double-helix Stable water clusters can be produced as disclosed herein. However this is only one kind of production.

The particle count of one such solution is displayed in the table.

TABLE 5 enhanced Solution S containing large number of double-helix structures with Material B Location: 01    SAMPLE SIZE: 1 ml    SYRINGE: 25 ml    TARE: 0.2 ml
Data is CUMULATIVE and NORMALIZED

| Date | Time | 0.1 | 0.15 | 0.2 | 0.25 | 0.3 | 0.35 | 0.4 | 0.5 |
|---|---|---|---|---|---|---|---|---|---|
| Mar. 1, 2009 | 16:29:08 | 163250 | 147920 | 112620 | 81360 | 44100 | 31800 | 26460 | 20500 |
| Mar. 1, 2009 | 16:29:09 | 167320 | 148300 | 113780 | 81080 | 42880 | 31060 | 25640 | 20120 |
| Mar. 1, 2009 | 16:29:10 | 161900 | 147380 | 111280 | 79700 | 42900 | 31540 | 26500 | 20640 |
| Run Results | | | | | | | | | |
| Mar. 1, 2009 | 16:29:10 | 162960 | 147867 | 112560 | 80713 | 43293 | 31467 | 26200 | 20420 |
| Run Complete OK | | | | | | | | | |

Thus stable water clusters can have helix structures, which can form in a double-helix shape. The double-helix structure can be precursor in the development of life before a DNA molecule was formed. The helix structure has a width of several microns size or several nanometers.

It will be understood that each of the elements described above, or two or more together, may also find a useful application in other types of constructions differing from the type described above.

While the invention has been illustrated and described as embodied in product with solid stable water clusters, it is not intended to be limited to the details shown, since various modifications and structural changes may be made without departing in any way from the spirit of the present invention.

Without further analysis, the foregoing will so fully reveal the gist of the present invention that others can, be applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A product, comprising solid stable water clusters including a plurality of water molecules connected with one another by electrical dipole interaction via internal electric field of ions and having a permanent electric dipole moment with an electrical field surrounding the solid stable water clusters.

2. A product as defined in claim 1, wherein said solid stable water clusters are stable under normal room temperature and atmospheric pressure.

3. A product as defined in claim 1, wherein the product contains further water with said solid stable water clusters in said water.

4. A product as defined in claim 1, wherein the product contains further a petroleum component with said solid stable water clusters.

5. A product as defined in claim 4, wherein the petroleum component is a component selected from the group consisting of gas, diesel, and natural gas.

6. A product as defined in claim 1, wherein the product contains further a skin care component with said solid stable water clusters contained in it.

7. A product as defined in claim 1, wherein the product contains further a component providing health benefits, with said stable solid water clusters contained in it.

8. A product as defined in claim 7, wherein the component providing health benefits is a component selected from the group consisting of vitamins, minerals, hormones and extracts.

9. A product as defined in claim 1, wherein the product contains further also an additional component, containing said solid stable water clusters, wherein said solid stable water clusters are in form of an emulsion that contains a suspension of small water droplets that include said solid stable water clusters.

10. A product as defined in claim 1, wherein said solid stable water clusters have a ring-shaped structure.

11. A product as defined in claim 10, wherein said solid stable water cluster have the ring-shaped structure selected from the group consisting of a pentagon, a hexagon, and a rectangle.

12. A product as defined in claim 10, wherein a plurality of the ring-shaped structures of said solid stable water clusters are joined together to form larger structures of said solid stable water clusters.

13. A product as defined in claim 12, wherein said larger structures of said solid stable water clusters are structures having a shape selected from the group consisting of a linear structure, a ring-shaped structure, a kidney-shaped structure, and a helix shape.

14. A product as defined in claim 1, wherein said solid stable water clusters are arranged in form of a double helix.

15. A product as defined in claim 1, wherein said solid stable water clusters have nanometer sizes.

16. A method of producing the product as defined in claim 1, comprising multiple dilution of a material in a quality water so as to produce said solid stable water clusters.

* * * * *